US005776676A

United States Patent [19]
Prasad et al.

[11] Patent Number: 5,776,676
[45] Date of Patent: Jul. 7, 1998

[54] HME1 NUCLEIC ACIDS AND PROBES

[75] Inventors: Gaddamanugu L. Prasad; Herbert L. Cooper, both of Rockville, Md.

[73] Assignee: The United States of America as represented by the Department of Health and Human Services, Washington, D.C.

[21] Appl. No.: 466,444

[22] Filed: Jun. 6, 1995

Related U.S. Application Data

[62] Division of Ser. No. 887,072, May 20, 1992, Pat. No. 5,424,191.

[51] Int. Cl.$^6$ .............................. C12Q 1/68; C07H 21/04
[52] U.S. Cl. .................. 435/6; 536/23.5; 536/24.3; 536/24.31; 536/24.33
[58] Field of Search .................. 435/6, 91.2; 536/23.5, 536/24.3, 24.31, 24.33

[56] References Cited

U.S. PATENT DOCUMENTS

| | | | |
|---|---|---|---|
| 4,707,438 | 11/1987 | Keydar | 435/5 |
| 5,597,719 | 1/1997 | Freed et al. | 435/194 |

OTHER PUBLICATIONS

Badley, et al. A simple, rapid method for the purification of poly A+ RNA. Biotechniques. 6: 114–116. (1988).

Ceriani, R., et al. Circulating human mammary epithelial antigens in breast cancer. Proc. Natl. Acad. Sci. USA 79:5420–5424. (1982).

Chou, P.Y. and G.D. Fasman. Prediction of protein confirmation. Biochemistry 13: 222–245. (1974).

Clark, R. et al. Transformation of human mammary epithelial cells by oncogenic retroviruses. Cancer Res. 48: 4689–4692. (1988).

Cooper, H.L. et al. Post–translational formation of hypusine in a single major protein occurs generally in growing cells and is associated with activation of lymphocyte growth. Cell 29:791–797. (1982).

Fuchs, E., Keratins as biochemical markers of epithelial differentiation. Trends Gen. 4: 277–281. (1988).

Hammond, S.L. et al. Serum–free growth of human mammary epithelial cells: rapid clonal growth in defined medium and extended serial passage with pituitary extract. Proc. Nat. Acad. Sci. U.S.A. 81:5435–5439. (1984).

Huse, W. et al. Generation of a large combinatorial library of the immunoglobulin repetoire in phage lambda. Science 246:1275. (1989).

Ichimura, T. et al. Molecular cloning of cDNA coding from brain specific 14-3-3 protein, a protein kinase–dependent activator of tyrosine and tryptophan hydroxylases. Proc. Nat. Acad. Sci. USA 85:7084–7088. (1988).

Imrie, S.F. et al. Detailed investigation of the diagnostic value in tumor histopathology of ICR2, a new monoclonal antibody to epithelial membrane antigen. Histopathology 16: 573–581. (1990).

Kohler, G. and C. Milstein. Continuous culture of fused cells secreting antibody of predefined specificity. Nature (London) 256:495–497. (1975).

Kozak, M. Structural features in eukaryotic mRNAs that modulate the initiation of translation. J. Biol. Chem. 266:19867–19870. (1991).

(List continued on next page.)

*Primary Examiner*—Kenneth R. Horlick
*Attorney, Agent, or Firm*—Knobbe, Martens, Olson & Bear

[57] ABSTRACT

A full length cDNA clone from a normal human mammary epithelial cell (strain 184) encoding a 25 kDa protein, HME1, was isolated. Expression of HME1 RNA appears to be limited to epithelial cells. The HME1 sequence shares strong sequence homology with bovine 14-3-3 protein, which is an activator of tyrosine and tryptophan hydroxylase, but the tissue distribution of HME1 differs from that of 14-3-3. Compared with normal mammary epithelial cells, expression of HME1 RNA is dramatically low in cells derived from human mammary carcinoma and in normal mammary epithelial cells transformed by oncogenes. HME1 therefore appears to be a cellular differentiation marker that is down-regulated during neoplastic transformation.

10 Claims, 6 Drawing Sheets

```
         ♦     10        20        30        40        50        60 ♦
ME-RASLIQKAKLAEQAERYEDMAAFMKGAVEKGEELSCEERNLLSVAYKNVVGGQRAAWRVLSSIEQKS
MGDREQLLQRARLAEQAERYDDMASAMKAVTELNEPLSNEDRNLLSVAYKNVVGARRSSWRVISSIEQKT
         10        20        30        40        50       ♦60 ♦       70

70        80        90       100       110       120       130
NEEGSEEKGPEVREYREKVETELQGVCDTVIGLLDSHLIKEAGDA--ESRVFHLKMKGDYYRYLAEVATG
MADGHEKKLEKVKAYREKIEKELETVCNDVLALLDKFLIKNCNDFQYESKVFYLKMKGDYYRYLAEVASG
         80        90       100       110       120       130       140

140       150       160       170    I  180       190     ♦ 200
DDKKRIIDSARSAYQEAMDISKKEMPPTNPIRLGLALNFSVFHYEIANSPEEAISLAKTTFDEAMADLHT
EKKNSVVFASEAAYKEAFEISKEHMQPTHPIRLGLALNFSVFYYEIQNAPEQACLLAKQAFDDAIAELDT
         150       160       170       180       190       200       210

210       220    I  230       240
LSEDSYKDSTLIMQLLRDNLTWTADNAGEEGGEVPQEPQG  - HME1
LSEDSYKDSTLIMQLLRDNLTLWTSDQQDEEAGEGN     - BOV14-3-3
         220       230       240
```

OTHER PUBLICATIONS

Laemmli, U.K. Cleavage of structural proteins during the assembly of the head of bacteriophage T4. Nature. London. 227:680–685. (1970).

Maniatis, T., E.F. Fritsch and J. Sambrook. Molecular Cloning. 2nd Edition. Cold Spring Harbor N.Y., Cold Spring Harbor Laboratory. (1989).

Merrick, W. Meth. Enzymol. 101:38. (1983).

Mullis, K., and Faloona, F. Meth. Enzymol. 155:335. (1987).

O'Brian, C.A. et al. Elevated Protein Kinase C expression in human breast tumor biopsies relative to normal breast tissue. Cancer Res. 49:3215–3217. (1989).

Patten, B.M. et al. Foundations of embryology. 3rd Ed., McGraw Hill, N.Y. (1974).

Pinkus, G.S. and P.J. Kurtin. Epithelial membrane antigen–a diagnostic discriminant in surgical pathology. Human Pathology 16: 929–940. (1985).

Prasad, G.L. et al. A cDNA encoding a muscle–type tropomyosin cloned from a human epithelial cell line: identity with human fibroblast tropomyosin TM1. Biochem. Biophys. Res. Commun. 177:1068–1075. (1991).

Rosenfeld, G.C. et al. Cloning, distribution and expressing of rat 14–3–3 protein. FASEB J. 5:A834. (1991).

Sanger, F. et al. DNA sequencing with chain–terminating inhibitors. Proc. Nat. Acad. Sci. U.S.A. 75:5463–5467. (1977).

Sasaki, M. et al. Breast cancer markers: comparison between sialyltransferase and human mammary epithelial antigens (HME–Ags) for the detection of human breast tumors grafted in nude mice. Breast Cancer Res. and Treatment 5:51–56. (1985).

Schejter, E.D. and B.Z. Shilo. The drosophila EGF receptor homolog. DER. gene is allelic to faint little ball, a locus essential for embryonic development. Cell 56:1093–1104. (1989).

Schejter, E.D. et al. Alternative 5' exons and tissue specific expression of Drosophila EGF receptor homolog transcripts. Cell 46:1091–1101. (1986).

Shibuya, M. et al. Nucleotide sequence and expression of a novel human receptor–type tyrosine kinase gene, flt, closely related to the fms family. Oncogene 5:519–524. (1990).

Soule, H.D. et al. Isolation and characterization of a spontaneously immortalized human breast epithelial cell line, MCF–10. Cancer Res. 50: 6075–6086. (1990).

Stampfer, M.R. Isolation and growth of human mammary epithelial cells. J. Tissue Culture Meth. 9: 107–115. (1985).

Stampfer, M.R. and J.C. Bartley. Induction of transformation and continuous cell lines from normal human mammary epithelial cells after exposure to benzo[a]pyrene. Proc. Nat. Acad. Sci. U.S.A. 82:2394–2398. (1985).

Toker, A. et al. Protein Kinase C inhibitor proteins: Purification from sheep brain and sequence similarity to lipocortins and 14–3–3 protein. Eur. J. Biochem. 191: 421–429. (1990).

Prasad, et al., (1991), *FASEBJ*, 5(6), A1650, No. 7432.

Nielson (1991), *Biochem. Biophys. Acta.* 1088, 425–428.

Zupan, et al. (1992), *J. Biol. Chem.* 267(13), 8707–8710.

```
                    ◆                                              60      ◆
       ME-RASLIQKAKLAEQAERYEDMAAFMKGAVEKGEELSCEERNLLLSVAYKNVVGGQRAAWRVLSSIEQKS
       MGDREQLLQRARLAEQAERYDDMASAMKAVTELNEPLSNEDRNLLSVAYKNVVGARRSSWRVISSIEQKT
                10        20        30        40        50    ◆   60        70

ESRVFHLKMKGDYYRYLAEVATG
       NEEGSEEKGPEVREYREKVETELQGVCDTVLGLLDDSHLIKEAGDA--ESRVFHLKMKGDYYRYLAEVATG
       MADGNEKKLEKVKAYREKIEKELETVCNDVLALLDKFLIKNCNDFQYESKVFYLKMKGDYYRYLAEVASG
                80        90       100       110       120       130       140

◆                      200
       DDKKRIIDSARSAYQEAMDISKKEMPPTNPIRLGLALNFSVFHYEIANSPEEAISLAKTFDEAMADLHT
       EKKNSVVEASEAAYKEAFEISKEHMQPTHPIRLGLALNFSVFYYEIQNAPEQACLLAKQAFDDAIAELDT
                150       160       170  ↑   180       190       200       210

↑    230               240
       LSEDSYKDSTLIMQLLRDNLTLWTADNAGEEGGEVPQEPQS     - HMEI
       LNEDSYKDSTLIMQLLRDNLTLWTSDQQDEEAGEGN          - BOV14-3-3
                220       230       240
```

FIG. 3

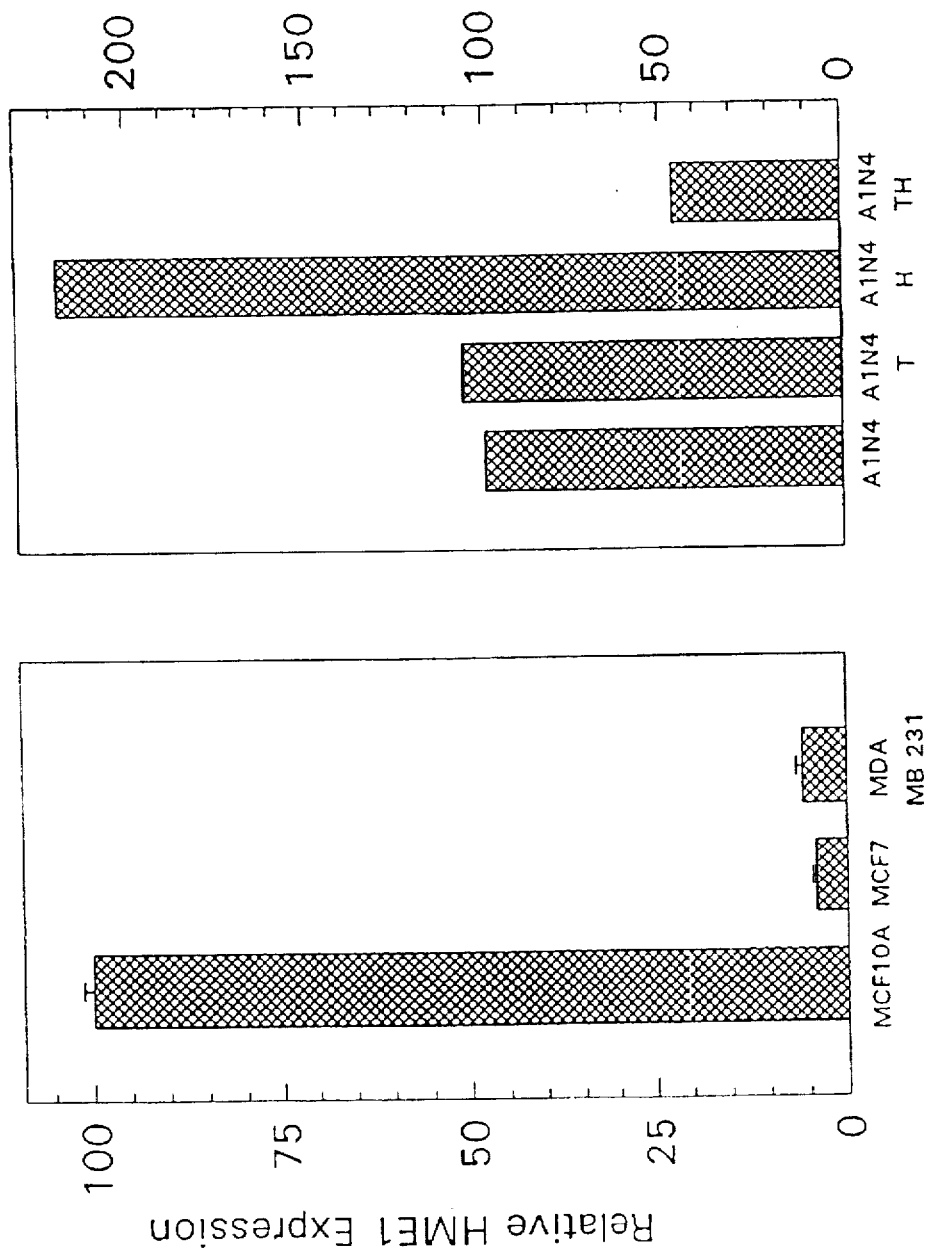

HME1 NUCLEIC ACIDS AND PROBES

This application is a divisional of application Ser. No. 07/887,072, filed May 20, 1992, now U.S. Pat. No. 5,424,191.

BACKGROUND OF THE INVENTION

The invention relates to cell markers that are useful in detecting disease; it relates particularly to cell markers that are useful in identifying epithelial cells and determining the differentiation status of normal and malignant epithelial cells.

The identification and characterization of epithelial cell markers is pursued in efforts to understand the biology of tissue differentiation and to diagnose and monitor carcinomas resulting from the malignant transformation of epithelial tissues.

Efforts to reduce the mortality resulting from breast cancer include the identification of breast tissue specific antigens, which are potentially useful in non-invasive methods leading to the early diagnosis of the disease and reliable follow up after surgical removal of tumors; they should also prove useful as well as a tool of basic research directed to breast cancer biology.

The use of high-prevalence, specific human mammary epithelial antigens (HME-Ags) as breast cancer markers has been proposed (Ceriani, et al., 1982); Sasaki et al., 1985). These antigens are localized in the plasma membranes of breast epithelial cells, whether the cells are normal or neoplastic, and they occur in all neoplastic breast cells. The antigens are normally released from the epithelial cells in the human milk fat globule membrane, but are also released into the circulation by mammary tumors. Breast cancer patients therefore have high levels of HME-Ags in circulating plasma, while patients with disseminated nonbreast cancer and normal females do not. Circulating antigens are found to have molecular weights of 150,000, 70,000, and 46,000 daltons.

A group of well characterized markers for epithelial cells of all tissue types is a family of proteins known as cytokeratins (Fuchs, 1988). Cytokeratins are the intermediate filament proteins of epithelial cells, and their presence is a definitive proof that the cells under study are of epithelial type; however, there are different members of cytokeratins, and their expression has been shown to be variable, and dependent on several parameters, including the tissue type and state of differentiation, so that their expression patterns may be complex and difficult to interpret. Another epithelial marker, epithelial membrane antigen, has been defined only in terms of immunological reactivity, which resides in the large (50%) carbohydrate moiety of the glycoprotein (Pinkus, et al, 1985). The primary use of this marker has been in distinguishing between tumors of epithelial and non-epithelial origin in histopathological sections, but it appears to be expressed also on various normal tissues of mesodermal origin, including fibroblasts (Imrie, et al., 1990). Cloning of the mRNA coding for the protein has not been reported.

It would be useful to identify a discrete epithelial cell specific marker that reliably follows cell differentiation, is not organ or tissue specific, but cell origin specific, and is associated only with epithelial cells, and not with cells from the fibroblast or lymphoid lineage. This marker could therefore be used to follow the extent of differentiation of epithelial cells or the extent of de-differentiation that occurs on neoplastic transformation. A specific epithelial cell marker could also determine whether tumors are of epithelial origin or not, a distinction which is often important in therapy.

SUMMARY OF THE INVENTION

The invention provides an enriched or isolated oligonucleotide sequence identified as SEQ ID NO:1. The invention includes allelic variation of SEQ ID NO:1 or a complementary sequence or sequential subsets of SEQ ID NO:1 at least 15 nt in length. The invention also includes an isolated or enriched oligonucleotide operably coding for a human gene product which includes a gene sequence coding for the same amino acid sequence as the coding sequence of a gene corresponding to a sequence designated as SEQ ID NO:1. The invention also includes an enriched or isolated oligonucleotide sequence, corresponding to a human gene, which hybridizes to the sequence designated as SEQ ID NO:1, or to a sequence complementary thereto, under hybridization conditions sufficiently stringent to require at least 90% base pairing. Any of the oligonucleotides described above can be in substantially purified form.

According to another aspect of the invention there are provided probes useful for identifying a specific marker for human epithelial cells in tissues or fluids of the body. The probes comprise a detectable signal-producing labelled oligonucleotide of at least about 15 nucleotide bases that is complementary to a gene sequence designated as SEQ ID NO: 1, or a specific subset thereof, and hybridize with the gene sequence to produce a labelled oligonucleotide duplex.

According to yet another aspect of the invention there is provided an essentially pure protein, designated HME1, and encoded by a DNA sequence having SEQ ID NO:1. Alternatively, the invention provides an enriched or isolated HME1 polypeptide having an amino acid sequence designated as SEQ ID NO:2, or a sequential subset thereof at least 6 amino acids in length.

The invention also provides antibodies that specifically bind to the polypeptide designated as SEQ ID NO:2, or fragments that are sequential subsets thereof; the antibodies can be either polyclonal or monoclonal, and recognize epitopes or antigenic determinants of SEQ ID NO:2.

According to another aspect of the invention there are provided methods for identifying epithelial cells and for determining neoplastic transformation of epithelial cells by means of the detection and quantitation of the HME1 genetic sequences using the signal-producing labelled oligonucleotide probes of the invention.

According to one embodiment of the method, a dot blot procedure, an RNA preparation is placed on a membrane and fixed thereto; then the membrane and the fixed RNA are contacted with a signal-producing labelled probe having a nucleotide sequence of at least about 15 bases and at least substantially complementary to a nucleotide sequence of HME1 under hybridizing conditions of a predetermined stringency; and duplex formation, indicating the presence of HME1 RNA, is determined on said membrane by means of said signal.

According to another embodiment of this aspect of the invention, the level of HME1 expression in a sample of human tissue is determined by an electrophoretic separation of an RNA preparation from a sample of tissue, followed by transfer of the separation pattern to an immobilizing membrane by blotting. The membrane with the transferred RNA is then contacted with the signal-producing labelled probe complementary to HME1 RNA as described above. HME1 RNA in an RNA preparation isolated from a tissue sample is also determined, according to a method of the invention, by contacting the RNA-containing preparation with a signal-producing labelled probe at least about 100 nucleotide bases in length and having a nucleotide sequence substantially complementary to the coding sequence of SEQ ID NO: 1, whereby HBE1 RNA in said preparation is bound to said probe, and then digesting single-stranded nucleotide sequences in said preparation by means of a nuclease enzyme specific for said sequences. The digested sample is then separated by electrophoresis and the level of duplex formation in said electrophoretically separated sample is determined by means of the signal-labelled probe.

The invention also provides a method of detecting HME1 epithelial marker protein or fragments thereof in the cells of a human tissue specimen according to immunohistochemical methods, comprising contacting a fixed or frozen tissue specimen suspected of containing epithelial cells with monoclonal or polyclonal antibodies having a signal-producing label and measuring the level of HME1 marker protein by means of the formation of antigen-antibody complexes according to the signal provided by the labelled antibody. Alternatively, nucleic acid sequences specific to HME1 can be detected in the tissue specimen by the binding thereto of the labelled nucleotide sequence or probe described above, and measuring the signal following duplex formation between the specific nucleic acid sequences and the probe.

BRIEF DESCRIPTION OF THE DRAWINGS

FIGS. 1A–1B. The nucleotide sequence of HME1 and comparison with that of bovine 14-3-3 protein. The sequence complementary to the oligonucleotide probe, beginning at nt 474, is singly underlined. Initiation site, terminator, polyadenylation site and the GT repeat are doubly underlined A.5'end. B.3'end.

FIG. 3. Comparison of the derived amino acid sequences of HME1 and Bovine 14-3-3 protein. HME1 is shown as the upper sequence. *: amino acid identity; |: conservative substitution; ♦: potential phosphorylation sites; ↓: potential N-glycosylation sites. Regions identical to PK-c inhibitory peptides (Toker, et al., 1990) are underlined.

FIGS. 5A and 5B. Levels of HME1 RNA in normal and transformed mammary cells. HME1 expression was determined by quantitation of the radioactive signal on northern blots. Values were normalized to the actin signal determined from the same blot. Results are expressed relative to the value obtained for normal mammary cells. 5A. Comparison of normal human mammary epithelial cells (MCF10A) with cells derived from spontaneous breast carcinomas. 5B. Comparison of immortalized normal human mammary epithelial cells (184A1N4) with derivatives of that line expressing SV40-T (A1N4-T), v-Ha-ras (A1N4-H), and both SV40-T and v-Ha-ras (A1N4-TH).

DETAILED DESCRIPTION OF THE INVENTION

Figure 2:
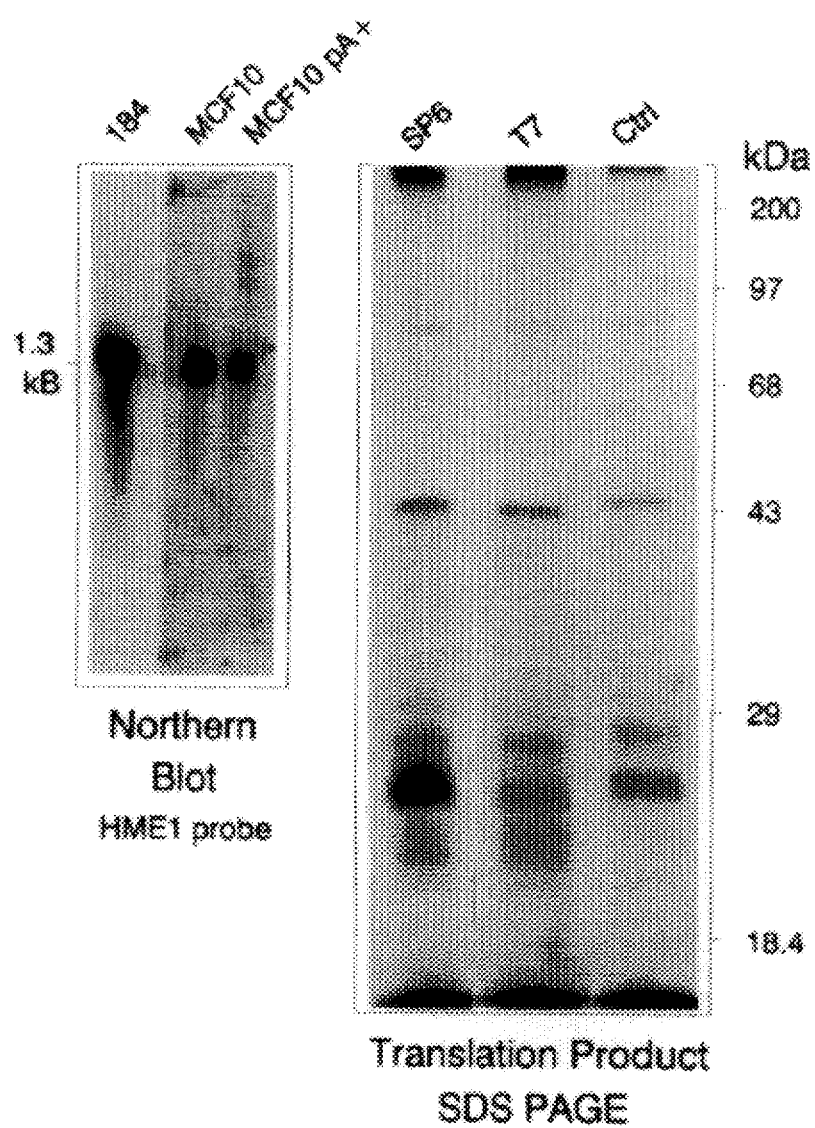
FIG. 2. Expression of HME1 RNA in 184 and MCF10A normal human mammary epithelial cells and cell-free translation product. Left Panel. Northern blot probed with full-length HME1 cDNA. Left Lane: 184 cell total RNA, 40 µg; Center lane: MCF10A total RNA, 40 µg; Right lane; MCF10A poly(A) +RNA, 4 µg. Right Panel: In vitro translation products. HME1 cDNA was cloned into the pGEM7Zf+ vector, transcribed in both orientations and capped (Promega Biotech system, Promega, Madison, Wis. 53711). RNA was translated in rabbit reticulocyte lysate and products analyzed by 1-dimensional PAGE followed by fluorography. Left lane: SP6 polymerase RNA product, showing specific 25 kDa protein encoded by RNA produced in this orientation; Center lane: T7 polymerase RNA product; Right lane: control, no RNA added.

A heretofore unknown cDNA, designated HME1, was isolated and characterized from a normal mammary epithelial cDNA library. This gene appears to have a selective expression pattern: it was detected only in cells of epithelial type originating from all the three primordial germ layers, ectoderm, entoderm and mesoderm (Patten, et al., 1974).

HME1 was first identified during the screening of a normal human mammary epithelial cell (strain 184) cDNA library with an oligonucleotide complementary to a region of human tropomyosin. The cross-reacting cDNA clone (HME1) was unrelated to tropomyosin but possessed unique and interesting properties. The isolated 1300 bp insert from this clone specifically hybridizes to a 1.3 kb RNA isolated from cell strain 184, suggesting that HME1 is a full-length, or near full-length, clone. Its nucleotide sequence shows no significant homology to tropomyosin (Prasad, et al., 1991) and is not identical to any sequence in the data base, although a related sequence was noted. The expression pattern of HME1 in different cell types indicated that it was preferentially expressed in epithelial cells and was down-regulated on neoplastic transformation. The description that follows, and the attached examples present a characterization of the HME1 clone and detail its expression in cultured cells of different types. A nucleotide sequence listing for HME1 is incorporated herein as SEQ ID NO:1; an amino acid sequence listing for HME1 protein is incorporated herein as SEQ ID NO:2. The GENBANK accession number for HME1 is M93010.

Cell Types in which HME1 is Expressed

HME1 was initially identified in a cDNA library synthesized from Strain 184 cells, and a full length cDNA clone isolated according to the procedure in Example 1. The Strain 184 cells are primary diploid normal human mammary epithelial cells derived from a reduction mammoplasty and retain many biochemical characteristics of mammary epithelial cells, including expression of epithelial-specific cytokeratin (Hammond, et al., 1984; Stampfer, 1985).

Expression of HME1 was also found in various cell lines, as indicated in Table 1. Normal mammary cell lines expressing HME1 include 184A1N4 and MCF10A. Line 184A1N4 is a near-triploid subclone of line 184A1, which is an immortalized line derived from 184 cells by treatment with benzo[a]pyrene. Neither 184 cells nor 184A1N4 cells are tumorigenic in nude mice, nor do they exhibit anchorage-independent growth in culture (Clark, et al., 1988; Stampfer, 1985). Both of these were obtained from Martha Stampfer, Berkeley, Calif. and cultured as described (Hammond, et al., 1984).

MCF10A cells (ATCC No. CRL 10317) are an immortalized line of human mammary epithelial cells that are near-diploid and exhibit no characteristics of neoplastic transformation (Soule, et al., 1990). They were provided by J. Russo, Michigan Cancer Foundation, Ann Arbor, Mich.

HME1 was also found in mammary carcinoma cell lines MDA MB 231 (ATCC No. HTB26); T47D (ATTC No. HTB 133); MCF7 (ATCC No. HTB 22) and breast carcinosarcoma HS578T (ATCC No. HTB 126). Other human sources of HME1 are colon carcinoma lines LS174T (ATCC No. CL 188); HT 29 (ATCC No. HTB 38); and WiDr (ATCC No.

CCL 218); liver carcinoma line Sk-Hep-1 (ATCC No. HTB 52); lung carcinoma line A-427 (ATCC No. HTB 53); bladder carcinoma line SCaBER (ATCC No. HTB 3); kidney carcinoma line CAKI-2 (ATCC No. HTB 47); and ovarian carcinoma line Caov-3 (ATCC No. HTB 75). All cells other than the 184, 184 A1N4, and MCF10A were purchased from ATCC, Rockville, Md., and grown as specified.

Isolation and Characterization of a HME1 cDNA Clone

Figure 1A:
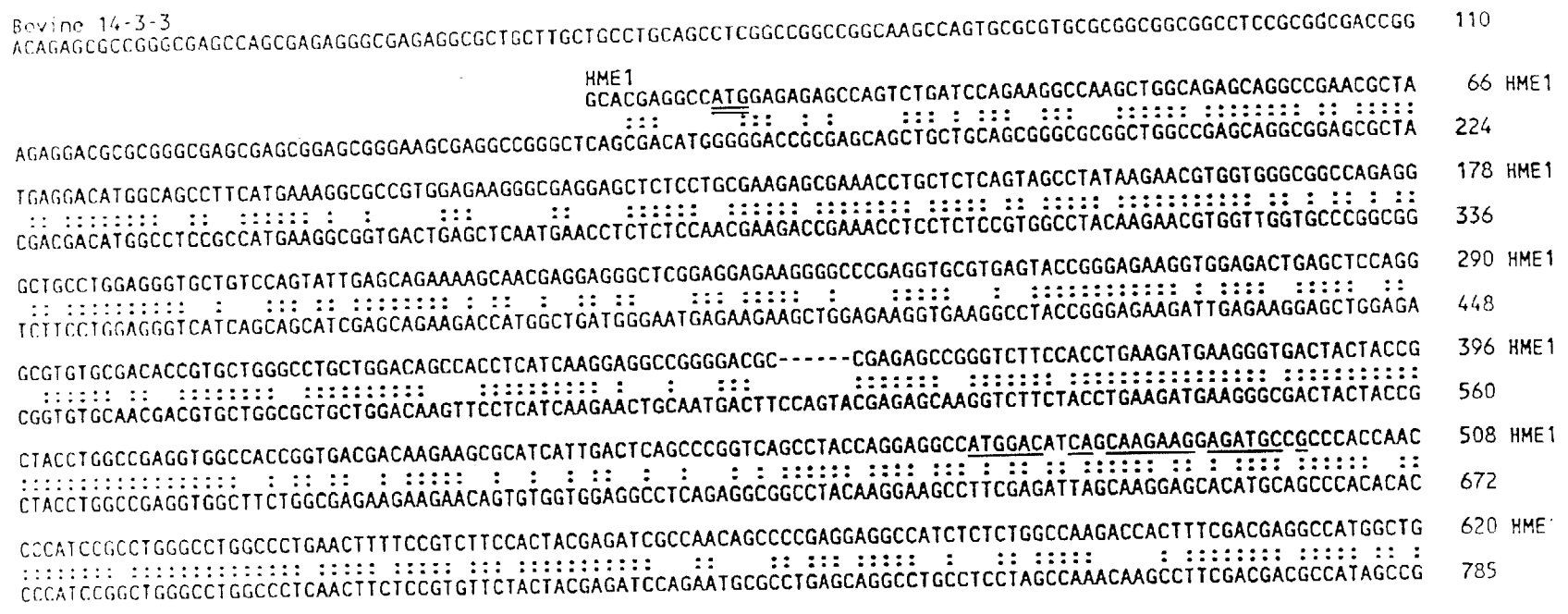

The HME1 cDNA clone was isolated in the course of an attempt to isolate an epithelial specific tropomyosin using as a probe an oligonucleotide that appears to be present in all the muscle type tropomyosin isolated so far. The 1.3 kb clone we obtained, isolated as described in Example 1, did not hybridize to tropomyosin mRNA at high stringency (0.1× SSC and 1% SDS at 65° C.). Upon sequencing, it was revealed that the clone was not a tropomyosin, but a novel clone with a unique sequence. The cDNA clone has a total of 1245 nt (FIG. 1). Following the short 5'-untranslated sequence there is an open reading frame of 744 nt followed by 491 nt of 3'-untranslated region. The ATG initiation codon is preceded by Kozak's consensus sequence (Kozak, 1991). The polyadenylation signal is at position 1221 followed by a poly(A) tail of about 30 residues. The oligodeoxynucleotide we employed to isolate this clone resembles a short stretch of nucleotides beginning at position 474, which may be the basis for hybridization to HME1 at low stringency. In the 3'-untranslated region a 36 nt alternating sequence, GTGTGT. . . , occurs. Extended GT repeats are a common motif, found in intron regions of many genes, and occasionally in the 3'-untranslated region of mRNA (Shibuya, et al., 1990). The function of this repeat, if any, is unknown.

The isolated cDNA specifically hybridized to a 1.3 kb RNA from strain 184 cells (FIG. 2) which suggests that this may be a full length clone. It hybridized to a species of identical size in RNA from line MCF10A, another normal human mammary epithelial cell. When HME1 cDNA was subcloned into a Gemini vector and the RNA transcribed from it was translated in vitro, a 25 kDa protein was produced whose $M_r$ is in agreement with that of the $M_r$ obtained from the derived amino acid sequence of HME1 cDNA (FIG. 2).

Sequence Homologies

HME1 shares extensive sequence homology with bovine 14-3-3 protein (Ichimura, et al., 1988). A nucleotide sequence listing for the bovine 14-3-3 protein is incorporated herein as SEQ ID NO:3. The latter protein was originally described as a brain-specific protein implicated in the regulation of monoamine biogenesis (Ichimura, et al., 1988). It has been shown to be a kinase II dependent activator for tryptophan and tyrosine hydroxylases (FIG. 1). These enzymes play an important regulatory role in the biogenesis of monoamines and neurotransmitters. Subsequent studies (Rosenfeld, et al., 1991) showed that this protein is present in other tissues such as skeletal muscle and erythrocytes, and other unknown functions for 14-3-3 protein were proposed. Despite the strong sequence homology between these two cDNAs, we have failed to detect the 1.8 kb 14-3-3 RNA in our northern blots screened with HME1 cDNA at high stringency but, at lower stringency, we have occasionally noticed a cross reacting species at that position. The bovine protein is encoded by a larger, 1.8 kb RNA (Ichimura, et al., 1988) and, contrary to the original reports, its expression is not limited to brain (Rosenfeld, et al., 1991). A comparison between the two sequences indicates that they may be part of the same gene family. Also we have not observed cross hybridizing multiple RNA species in northern blots with the HME1 probe as reported for rat 14-3-3 protein (Ichimura, et al., 1988; Rosenfeld, et al., 1991). Including conservative amino acid substitutions, the derived amino acid sequences of cDNAs for HME1 and 14-3-3 show over 70% identity. Significantly, however, the potential phosphorylation sites and the distribution of charged amino acids differ for the two proteins. The derived amino acid sequence of HME1 also contains short peptide sequences (FIG. 3) that are nearly identical to those obtained from purified fractions of sheep brain showing protein kinase-c (PK-c) inhibitory activity (Toker, et al., 1990). The same sequences were reported to be present in members of the lipcortin family (Toker, et al., 1990). While the precise relationship between HME1 and these other groups remains to be investigated, the presence of these peptide sequences in HME1 raises the possibility that HME1 may play a role in PK-c regulation. In this regard, it may be significant that PK-c activity has been reported to be elevated in neoplastically transformed cells .(O'Brian, et al., 1989), which are the types of cells in which HME1 expression is reduced. Taken together, its sequence similarities to both an activator for specific regulatory enzymes and an inhibitor of protein kinase c prefigure a role for HME1 as an intracellular regulatory molecule.

These observations, together with the apparent differences in tissue distribution, suggest that HME1 and 14-3-3 protein are derived from related but distinct members of a gene family whose products serve different physiological functions.

The similarity between the derived amino acid sequences is also extensive (FIG. 3). An amino acid sequence listing for the bovine 14-3-3 protein is incorporated herein as SEQ ID NO:4. Of the 248 amino acids comprising HME1, 156 identities with bovine 14-3-3 are present, as well as more than 20 conservative amino acid substitutions. The HME1 protein is predominantly hydrophilic, with neither leader sequence nor potential transmembrane region, and it contains many charged amino acids. HME1 and 14-3-3 protein have two potential N-glycosylation sites in common, although it is not known whether either protein is glycosylated. It is therefore likely that, like the 14-3-3 protein (Ichimura, et al., 1988), HME1 is a soluble cytosolic protein. Computer models of the polypeptides suggest these two sequences might have similar secondary structures (Chou, et al., 1974). Notwithstanding these similarities, some notable differences also exist between the two polypeptides. As noted, they are encoded by different sized mRNAs. The pI of the $NH_2$-terminal ⅔ of the 14-3-3 protein is considerably less acidic than the COOH-terminal ⅓ (6.2 versus 3.2) which has led to speculations as to functional significance (Ichimura, et al., 1988); this difference is unimpressive in HME1 (4.97 versus 3.92). Potential phosphorylation sites for cAMP dependent protein kinase are found at serines 5 and 196 in HME1 but not at the corresponding sites in 14-3-3. A potential phosphorylation site at serine 59 of protein 14-3-3 is not present in HME1, while the two proteins share a potential site at serine 63 of HME1.

HME1 also displays significant homology with a sequence originally described as type III alternative 5' exon of the Drosophila melanogaster homolog (DER) of the epidermal growth factor receptor (Schejter, et al., 1986) over a stretch of the first 100 amino acids. Subsequently, this drosophila sequence was reported to be, in fact, unrelated to DER (Schejter, et al., 1989). Since no further details were provided, the significance of the homology cannot be assessed. It is possible that this sequence derives from the drosophila homolog to the gene family comprising HME1 and 14-3-3.

Expression of HME1 in Various Tissues

Figure 4:
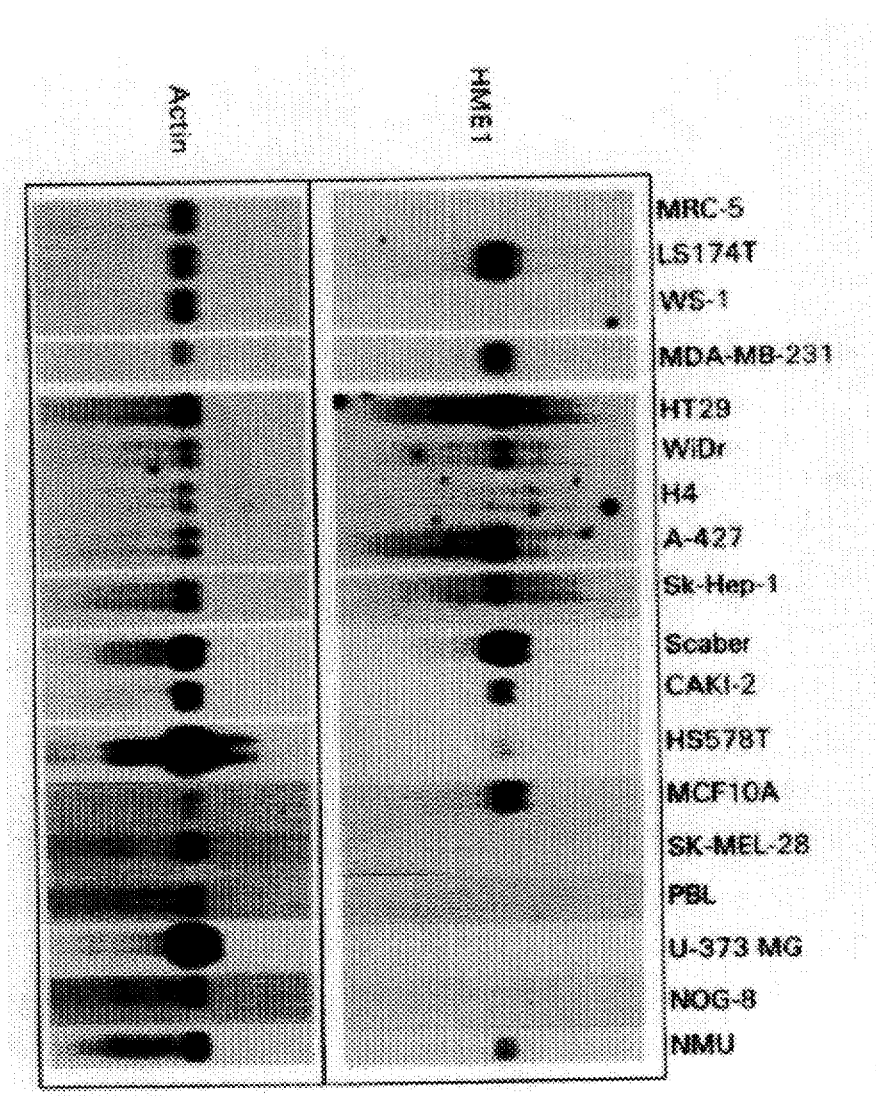
FIG. 4. Expression of HME1 RNA in various cell lines as analyzed by Northern blots. Poly(A)+RNA was probed with: A. Full length HME1 cDNA; B. Human β-actin cDNA.

Northern blot analysis was employed to investigate the distribution of HME1 in cells of different tissue origin (Table I, FIG. 4). The MCF10A cell line, which was developed from immortalized normal mammary epithelial cells, strongly expresses 1.3kb HME1 mRNA (FIGS. 2, 4). These are normal cells and do not grow as colonies in semisolid medium (Soule, et al., 1990). MDA MB 231, which is a spontaneously derived mammary carcinoma cell line, also expresses HME1 RNA in significant quantities. Two other cell lines derived from human breast carcinomas, T47D and MCF7, also express HME1.

All three colon carcinoma cell lines tested (LS174T, HT29 and WiDr) had significant expression of HME1 RNA, as did lung carcinoma cell line A-427, liver adenocarcinoma cell line SK-HEP-1, squamous carcinoma of bladder (Scaber), renal clear cell carcinoma (CaKi-2), and ovarian carcinoma (Cavo-3). The mammary carcinosarcoma cell line, HS578T, had barely detectable levels of HME1 RNA which could be detected only after using 7ug of poly(A)$^+$ RNA and prolonged autoradiography. This suggests that the level of HME1 expression might reflect the extent of epithelial differentiation of the cell type. The rat mammary carcinoma cell line, NMU, also elaborated 1.3 kb HME1 RNA, but NOG-8 mouse mammary epithelial cells did not, suggesting some degree of species restriction.

Expression of HME1 was not detected in nonepithelial cells such as fibroblasts, lymphocytes, glioblastoma or neuroglioma cells or in melanoma cells. However, the expression of HME1 could easily be detected as a single species in all the epithelial cells studied. In particular, HME1 is prominently expressed by normal mammary epithelial cells. All of the other epithelial cell types studied were derived from carcinomas, so it cannot be concluded with assurance that HME1 is expressed by the normal epithelia from which those carcinomas were derived, although the likelihood of such expression is great. HME1 expression appears to be a characteristic of normal and neoplastic human mammary epithelial cells and such expression distinguishes them from cells of the fibroblast or lymphoid lineages. The studies as described below, as well as the studies summarized in Table 1, support the conclusion that HME1 can be used as a general marker of epithelial differentiation.

Normal lung and skin fibroblasts (MRC5 and WS1, respectively) do not express HME1 RNA. Other cells which are not of epithelial origin, like peripheral blood lymphocytes, T cell leukemia (Molt4, blot not shown) and melanoma cells also do not express HME1 RNA. Significantly, the neuroglioma cells (H4) and glioblastoma (U373 MG) also are devoid of this RNA. Under the experimental conditions employed, there were not observed any other cross hybridizing RNAs along with HME1 as have been described in studies with bovine 14-3-3 (Ichimura, et al., 1988; Rosenfeld, et al., 1991).

Expression of HME1 RNA in Normal and Transformed Mammary Epithelial Cells

Since HME1 RNA is present in both normal and transformed mammary epithelial cells we explored the possibility of any quantitative differences in its expression in these cells. The two spontaneously transformed metastatic mammary carcinoma cell lines MCF-7 and MDA MB 231 express much lower levels of HME1 than the normal mammary epithelial cell line MCF10A (FIG. 5A). Thus, HME1 is strongly expressed in nontransformed human mammary epithelial cells (strain 184, line MCF10A, and line 184A1N4 (see below)), but is weakly expressed in lines derived from breast carcinomas.

HME1 RNA levels were quantitated in the normal (immortalized) epithelial cell line 184A1N4, which is derived from strain 184, and in 184A1N4 subclones expressing the v-Ha-ras oncogene (line 184A1N4-H), the SV-40-T antigen (line 184A1N4-T), and both of the preceding oncogenes (line 184A1N4-TH). Of these cell lines, only the doubly transfected line, 184A1N4-TH, has been reported to exhibit a frankly transformed phenotype (Clark, et al., 1988). We found that this transformed line expressed HME1 RNA at half the level of the nontransformed lines, 184A1N4 and 184A1N4-T (FIG. 5B). Unexpectedly, the other nontransformed line, 184A1N4-H expressed twice the control level of HME1 RNA. The significance of this increase is unknown. However, the observation remains that transformed mammary epithelial cells express reduced levels of HME1.

Thus, neoplastic transformation of mammary epithelial cells, whether arising spontaneously during carcinogenesis or induced by the action of transforming oncogenies, is associated with reduced expression of HME1.

The intermediate filament proteins of epithelial cells (cytokeratins), are widely accepted as the classical epithelial cell markers, but the multiple members of this group of cytoskeletal proteins present a highly complex and variable pattern of expression (Fuchs, 1988). On the other hand, HME1 is a single protein whose expression may also define epithelial differentiation but which presents fewer complications.

Down Regulation of HME1 in Neoplastic Transformation

Quantitative analysis revealed that spontaneously transformed mammary epithelial cells elaborate only 10–15% of the HME1 RNA of normal cells. In addition, among oncogene transfected mammary epithelial cells, the 184A1N4-TH cell line, which expresses the transformed phenotype, has decreased levels of HME1 RNA compared to the nontransformed parent 184A1N4 cell line. Evidently, in addition to being a marker of epithelial differentiation in mammary cells, HME1 expression is down-regulated in association with neoplastic transformation. As noted above, it has been reported that PK-c levels are elevated in tumor biopsies (O'Brian, et al., 1989). If HME1 were to function as an inhibitor of PK-c, as suggested by similarity in amino acid sequences, its decreased levels in the malignant cells might contribute to the reported elevation of enzyme activity in such cells.

Diagnostic Application of the HME1 Epithelial Marker

The reduction in HME1 expression associated with neoplastic transformation of epithelial cells can be useful as a diagnostic or prognostic indicator in clinical situations. The observation that the mammary carcinosarcoma line, HS578t, could be distinguished from other breast carcinoma lines by its very low expression of HME1 may serve as an example. HME1 can also serve as a marker to detect the metastasis of neoplastic epithelial tissue to sites where epithelial cells are physiologically absent, for example, in bone or lymphoid tissue.

The identification of the HME1 marker characteristic of epithelial cells or the determination of the level of HME1 expression in tissue can be accomplished qualitatively and quantitatively by analytic and diagnostic methods known to those skilled in the art for the detection of unique oligonucleotide sequences or unique polypeptide sequences. Such methods comprise the use of labelled DNA or RNA oligonucleotide probes that are complementary to HME1, to detect oligonucleotides having the sequence of SEQ ID NO:1 or fragments thereof which are sequential subsets of SEQ. ID NO:1 by means of the well known Northern or Southern blot techniques, as well as dot blot, slot blot and other nucleic acid transfer methods, and nuclease protection assays.

Examples of these methods are the Northern blot techniques as set forth in Examples 3 and 4; and a dot blot of an RNA preparation as set forth in Example 5. The labelled probes used in the blotting procedures are oligonucleotides complementary to HME1 having at least about 15 nucleotide bases. The ribonuclease protection method, wherein the level of HME1 expression in a sample of human tissue is determined by hybridizing RNA with a labelled probe to form a nucleotide duplex protected from subsequent ribonuclease digestion, is set forth in Example 6. The labelled probe used in the ribonuclease protection method is at least about 100 nucleotide bases in length.

HME1 antigen can be detected by means of antibodies, either polyclonal or monoclonal, having a specificity for the antigen represented by SEQ ID NO:2 or a fragment thereof which is a sequential subset of SEQ ID NO:2. Monoclonal antibodies to purified HME1 antigen are prepared by the classical hybridoma procedure of Kohler and Milstein, 1975, or by the recombinant method of Huse, 1989. The HME1 antigen used to raise the antibody can be prepared by known recombinant methods from the isolated cDNA clone, including amplification of the sequence using PCR techniques (Mullis, et al., 1987) and in vitro translation using reticulocyte lysate (Merrick, W., 1983), or using a commercial kit (Cat. No. 200360, Strategene Cloning Systems, La Jolla, Calif. 92037). Monoclonal antibodies and individual polyclonal antibodies can be specific to fragments of antigen of at least about 6 amino acids.

Probes used in the hybridizing procedures described or antibodies used in the antigen binding techniques described can bear signal producing label moieties such as a radioisotope, an enzyme that reacts with a substrate to produce a colored product, or a fluorescent molecule. Quantitation of the intensity of the signal can be made by direct measurement of radioactivity, densitometric measurement of an autoradiogram, optical density of colored enzyme product, or by fluorescence measurement of the bound labelled probe.

Labelled hybridizing probes can be used to detect HME1 sequences in nucleic acid preparations isolated from tissues. Fixed or frozen tissue sections can be examined with labelled nucleic acid probes, or with polyclonal or monoclonal antibodies according to any of the many known immunohistochemical methods as described for example, in Rose, et al., 1980. Immunochemical methods can also be applied to proteinaceous tissue extracts.

The cells of a biopsy or other tissue can be lysed and the nucleic acids and protein extracted in the lysate, which can be examined without electrophoresis, according to the dot blot procedure; or with preliminary electrophoresis, to accomplish the Northern or Southern blot for nucleic acid determinations, or the Western blot for antigen detection.

In the diagnostic applications described, samples of tissue comprising normal epithelial cells can be used as positive controls; nonepithelial tissue samples, such as lymphoid tissues, can be used as negative controls.

The genetic manipulations described below are disclosed in terms of their general application to the preparation of elements of the genetic systems of the invention. Occasionally, the procedure may not be applicable as described to each recombinant molecule included within the disclosed scope. The situations for which this occurs will be readily recognized by those skilled in the art. In all such cases, either the operations can be successfully performed by conventional modifications known to those skilled in the art, e.g. by choice of an appropriate alternative restriction enzyme, by changing to alternative conventional reagents, or by routine modification of reaction conditions. Alternatively, other procedures disclosed herein or otherwise conventional will be applicable to the preparation of the corresponding recombinant molecules of the invention. In all preparative methods, all starting materials are known or readily preparable from known starting materials. In the following examples, all temperatures are set forth uncorrected in degrees Celsius; unless otherwise indicated, all parts and percentages are by weight.

Without further elaboration, it is believed that one skilled in the art can, using the preceding description, utilize the invention to its fullest extent. The following preferred embodiments are, therefore, to be construed as merely illustrative and not limiting the remainder of the disclosure in any way.

EXAMPLE 1

RNA Preparation, Cloning and Screening

Total RNA (Maniatis, et al., 1989) and poly(A)$^+$RNA (Badley, et al., 1988) were isolated as described. cDNA was synthesized from cell strain 184 using a kit from Pharmacia LKB. The cDNA was ligated to dephosphorylated lambda-gt11 arms (Promega, Madison, Wis.) and packaged (Maniatis, et al., 1989). The cDNA library was screened with a synthetic oligodeoxynucleotide (TACCTGCGGTAGTTCTTCTTCTACGTCTAC), which is incorporated herein as SEQ ID NO:5 and 10 complementary to the initial portion of the coding sequence of nonmuscle tropomyosin-1 (Prasad, et al., 1991), at low stringency (final washing at 2× SSC +1% SDS at 38° C., 30 min., twice). SSC is 0.15M NaCl, 0.015M Sodium Citrate, pH 7.4. After three rounds of plaque purification, one of the isolated clones, HME1, was amplified by polymerase chain reaction (Perkin-Elmer-Cetus) using commercially available lambda primers (New England Biolabs). The reaction conditions were: denaturation at 94° C. for 2 min., annealing at 55° C. and extension at 72° C. for 2 min. and for 30 cycles. The amplified fragment was subcloned into pUC8 at the EcoR1 site and sequenced by the dideoxy method (Sanger, et al., 1977). Other molecular biological manipulations were done using standard protocols (Maniatis, et al., 1989).

EXAMPLE 2

In Vitro Translation

The isolated cDNA was subcloned into pGEM7zf+ vector (Promega) at the EcoR1 site and the sense and antisense RNAs were generated. The invitro transcribed RNAs were capped and translated in vitro using a rabbit reticulocyte lysate translation system (NEN) including [$^{35}$S]methionine. Translation products were separated on 12% SDS polyacrylamide gels and fluorographed (Cooper, et al., 1982); Laemmli, 1970).

EXAMPLE 3

Northern Blotting

Either poly (A)$^+$RNA (2–4 µg) or total RNA (20–40 µg) from a sample of tissue were separated on formaldehyde agarose gels and transferred to nylon membranes (Genescreen plus, New England Nuclear). Prehybridization was done for 6–8h in 6× SSC, 5× Denhardt's solution (Maniatis, et al., 1989), 0.1% sodium pyrophosphate, 100 μg/ml denatured salmon testis DNA, 1mM EDTA [ethylenediaminetetraacetate], 1% SDS [sodium dodecyl sulfate] and 50% deionized formamide at 37° C. followed by hybridization in the same solution overnight with random primer-labelled DNA fragments. The final stringency washes for HME1-probed membranes were done at 65° C. with 0.1% SSC and 1% SDS twice, each wash for 30 min. Actin-probed membranes were routinely washed at 50° C. with 2× SSC and 1% SDS twice for 30 min. each. Radioactivity on the membranes was quantitated with the Model 210 AMBIS Radioanalytic Imaging System (AMBIS Systems, San Diego, Calif.).

The expression of HME1 in various cell lines as determined by northern blot analysis is set forth in the following Table I.

TABLE I

Expression of HME1 in Various Cell Lines

| Tissue/cells | Normal/ Neoplastic | Cell Line | Embryologic Origin | HME1* |
|---|---|---|---|---|
| Mammary epithelium (human) | normal | Strain 184 | Ectoderm | + |
| | | MCF10A | | + |
| | | A1N4184 | | + |
| | carcinoma | MDA MB 231 | | + |
| | | T47D | | + |
| | | MCF7 | | + |
| | carcinosarcoma | HS578T | | ± |
| (mouse) | normal | NOG-8 | | − |
| (rat) | carcinoma | NMU | | + |
| Colon | carcinoma | LS174T | Endoderm | + |
| | | HT29 | | + |
| | | WiDr | | + |
| Liver | carcinoma | Sk-Hep-1 | Endoderm | + |
| Lung | carcinoma | A-427 | Endoderm | + |
| Bladder | carcinoma | Scaber | Endoderm | + |
| Kidney | carcinoma | CAKI-2 | Mesoderm | + |
| Ovarian | carcinoma | Cavo-3 | Mesoderm | + |
| Fibroblasts | normal | | Mesoderm | |
| | lung | MRC-5 | | − |
| | skin | WS-1 | | − |
| Lymphocytes | normal PBL | | Mesoderm | − |
| | T-cell leukemia | MOLT-4 | | − |
| Brain | neuroglioma | H4 | Mesoderm or ectoderm | − |
| | glioblastoma | U-373 MG | | − |
| Melanocyte | melanoma | SK-MEL-28 | Ectoderm (neural crest) | − |

*Determined by northern blot analysis.
With the exception of the mouse and rat lines noted, all lines derive from human tissue.

EXAMPLE 4

Northern Blot Assay for HME1 Down-Regulation in Tumor Tissue

Total RNA or poly (A)⁺RNA is isolated from excised epithelial tumors or metastases from these tumors using an RNA isolation kit (Invitrogen, San Diego, Calif.). The RNA is quantitated by spectrophotometer and aliquots are denatured by heating samples to 100° C. and blotted onto Nytran (Schleicher and Schuell, Keene, NH) in RNase free 2× SSC using a dot blot manifold (Bio Rad, Richmond, Calif.). Samples of 0.5, 1, 5 and 10 ug are blotted onto the manifold in duplicate together with equal quantities of RNA obtained from human fibroblasts (negative control). RNA samples from HeLa cells stably transfected with HME1 (positive control) in a suitable expression vector (such as PBPV, Pharmacia, Piscataway, N.J.) are blotted onto the manifold at a number of dilutions preferably beginning at 250 ng and ending at around 10 ug to permit relative quantitation of HME1-specific mRNA in the test samples. The wells of the manifold are rinsed in 2× SSC and the nucleic acid is linked to the filter using a Stratalinker™ (Stratagene, La Jolla, Calif.).

DNA probes corresponding to SEQ ID NO:1 or fragments which are sequential subsets thereof are end-labelled with $^{32}$P-dATP using polynucleotide kinase (Pharmacia, Piscataway, N.J.) following procedures described by Maniatis et al., *supra*, or alternatively, cDNA corresponding to SEQ ID NO: 1 is random primed and labelled with $^{32}$P-dCTP using a random priming DNA labelling kit (Boehringer-Mannheim, Indianapolis, Ind.).

The filter containing the RNA test samples is prehybridized and hybridized with 300 ng labelled probe using procedures described in Example 2. Following hybridization, filters are successively washed in 6× SSC and 1% SDS down to 2× SSC and 0.5% SDS. Filters are exposed to X-ray film (such as X-OmatAS, Eastman Kodak, Rochester, N.Y.).

EXAMPLE 5

Determination of HME1 Expression by Dot Blotting

A poly A RNA or total RNA preparation is obtained from a clinical tissue sample, and a measured quantity of the preparation is placed on a membrane support (Pharmacia, Piscataway, N.J.). The membrane is then contacted with a signal-labelled probe having a nucleotide sequence of at least about 15 nucleotide bases and substantially complementary to a nucleotide sequence coding for the protein of SEQ ID NO:2, under hybridization conditions of a predetermined stringency. The level of HME1 is determined by the level of duplex formation on the membrane as measured by the intensity of the signal on the labelled probe.

EXAMPLE 6

Determination of HME1 Expression by Ribonuclease Protection

RNA from a sample of human tissue is prepared in solution and hybridized to a signal-producing labelled probe that is complementary to the nucleotide sequence coding for the protein of SEQ ID NO:2, and at least about 100 nucleotide bases in length. Hybridization is carried out under conditions of about 90% stringency to form duplexes between the tissue HME1 RNA and the probe. Following hybridization, the sample is treated with a nuclease enzyme specific for single-stranded nucleic acids, for example, S1 nuclease (Boehringer-Mannheim, Indianapolis, Ind. 46250). After separation of the digested sample mixture by electrophoresis, the electrophoretic gel is dried, or alternatively, the separated nucleic acids are transferred to a blotting membrane. The level of HME1 in the separated sample is determined by the amount of duplex formed with the original probe by means of the signal-label of the probe.

LITERATURE CITED

Badley, J. E., G. A. Bishop, T. St. John and J. A. Frelinger. 1988. A simple, rapid method for the purification of poly A+ RNA. Biotechniques. 6: 114–116.

Ceriani, R., et al. 1982. Circulating human mammary epithelial antigens in breast cancer. Proc. Natl. Acad. Sci. USA 79:5420–5424.

Chou, P. Y. and G. D. Fasman. 1974. Prediction of protein confirmation. Biochemistry 13: 222–245.

Clark, R., M. R. Stampfer, R. Milley, E. O'Rourke, K. H. Whalen, M. Kriegler, J. Kopplin and F. McCormick. 1988. Transformation of human mammary epithelial cells by oncogenic retroviruses. Cancer Res. 48: 4689–4692.

Cooper, H. L., M. H. Park and J. E. Folk. 1982. Post-translational formation of hypusine in a single major protein occurs generally in growing cells and is associated with activation of lymphocyte growth. Cell 29: 791–797.

Fuchs, E. 1988. Keratins as biochemical markers of epithelial differentiation. Trends Gen. 4: 277–281.

Hammond, S. L., R. G. Ham and M. R. Stampfer. 1984. Serum-free growth of human mammary epithelial cells: rapid clonal growth in defined medium and extended serial passage with pituitary extract. Proc. Nat. Acad. Sci. U.S.A. 81:5435–5439.

Huse, W., L. Sastry, S. Iverson, and A. Kang. 1989. Generation of a large combinatorial library of the immunoglobulin repetoire in phage lambda. Science 246:1275.

Ichimura, T., T. Isobe, T. Okayama, N. Takahashi, K. Araki, R. Kuwano and Y. Takahashi. 1988. Molecular cloning of cDNA coding from brain specific 14-3-3 protein, a protein kinase-dependent activator of tyrosine and tryptophan hydroxylases. Proc. Nat. Acad. Sci. USA 85:7084–7088.

Imrie, S. F., J. P. Sloane, M. G. Ormerod, J. Styles and C. J. Dean. 1990. Detailed investigation of the diagnostic value in tumor histopathology of ICR2, a new monoclonal antibody to epithelial membrane antigen. Histopathology 16: 573–581.

Kohler, G. and C. Milstein. 1975. Continuous culture of fused cells secreting antibody of predefined specificity. Nature(London) 256:495–497.

Kozak, M. 1991. Structural features in eukaryotic mRNAs that modulate the initiation of translation. J. Biol. Chem. 266:19867–19870.

Laemmli, U. K. 1970. Cleavage of structural proteins during the assembly of the head of bacteriophage T4. Nature. London. 227:680–685.

Maniatis, T., E. F. Fritsch and J. Sambrook. 1989. Molecular Cloning. 2nd Edition. Cold Spring Harbor N.Y., Cold Spring Harbor Laboratory.

Merrick, W. 1983. Meth. Enzymol. 101:38.

Mullis, K., and Faloona, F. 1987. Meth. Enzymol. 155:335.

O'Brian, C. A., V. G. Vogel, S. E. Singletary and N. Ward. 1989. Elevated Protein Kinase C expression in human breast tumor biopsies relative to normal breast tissue. Cancer Res. 49:3215–3217.

Patten, B. M. and B. M. Carlson. 1974. Foundations of embryology, 3rd Ed., McGraw Hill, N.Y.

Pinkus, G. S. and P. J. Kurtin. 1985. Epithelial membrane antigen-a diagnostic discriminant in surgical pathology. Human Pathology 16: 929–940.

Prasad, G. L., S. Meissner, D. G. Sheer and H. L. Cooper. 1991. A cDNA encoding a muscle-type tropomyosin cloned from a human epithelial cell line: identity with human fibroblast tropomyosin TM1. Biochem. Biophys. Res. Commun. 177:1068–1075.

Rosenfeld, G. C., B. Sanborn and D. Loose-Mitchell. 1991. Cloning, distribution and expression of rat 14-3-3 protein. FASEB J. 5:A834.

Sanger, F., S. Nicklen and A.R. Coulson. 1977. DNA sequencing with chain-terminating inhibitors. Proc. Nat. Acad. Sci. U.S.A. 75:5463–5467.

Sasaki, M., Barber, S., and Ceriani, R. 1985. Breast cancer markers: comparison between sialyltransferase and human mammary epithelial antigens (HME-Ags) for the detection of human breast tumors grafted in nude mice. Breast Cancer Res. and Treatment 5:51–56.

Schejter, E. D. and B. Z. Shilo. 1989. The drosophila EGF receptor homolog, DER. gene is allelic to faint little ball, a locus essential for embryonic development. Cell 56:1093–1104.

Schejter, E. D., D. Segal, L. Glazer and B. Z. Shilo. 1986. Alternative 5' exons and tissue specific expression of Drosophila EGF receptor homolog transcripts. Cell 46: 1091–1101.

Shibuya, M., S. Yamaguchi, A. Yamane, T. Ikeda, A. Tojo, H. Matsushima and M. Sato. 1990. Nucleotide sequence and expression of a novel human receptor-type tyrosine kinase gene, flt. closely related to the fms family. Oncogene 5: 519–524.

Soule, H. D., T. M. Maloney, S. R. Wolman, W. D. Peterson, R. Brenz, C. M. McGrath, J. Russo, R. J. Pauley, R. F. Jones and S. C. Brooks. 1990. Isolation and characterization of a spontaneously immortalized human breast epithelial cell line, MCF-10. Cancer Res. 50: 6075–6086.

Stampfer, M. R. 1985. Isolation and growth of human mammary epithelial cells. J. Tissue Culture Meth. 9: 107–115.

Stampfer, M. R. and J. C. Bartley. 1985. Induction of transformation and continuous cell lines from normal human mammary epithelial cells after exposure to benzo [a]pyrene. Proc. Nat. Acad. Sci. U.S.A. 82:2394–2398.

Toker, A., C. A. Ellis, L. A. Sellers, and A. Aitken. 1990. Protein Kinase C inhibitor proteins: Purification from sheep brain and sequence similarity to lipocortins and 14-3-3 protein. Eur. J. Biochem. 191: 421–429.

There will be various modifications, improvements, and applications of the disclosed invention that will be apparent to those of skill in the art, and the present application is intended to cover such embodiments; therefore, it is intended that the full scope of these be measured by reference to the scope of the following claims.

---

What is claimed is:

1. An isolated oligonucleotide comprising a nucleotide sequence encoding the HME1 protein as shown in SEQ ID NO: 1, or a sequential subset thereof being at least 15 nucleotides in length, or a complementary sequence thereto, provided that said oligonucleotide is not a sequential subset of the nucleotide sequence encoding the Bovine 14-3-3 protein as shown in SEQ ID NO:3.

2. An isolated oligonucleotide comprising a nucleotide sequence encoding the HME1 protein having the amino acid sequence as shown in SEQ ID NO: 2, or a sequential subset thereof being at least 15 nucleotides in length, or a complementary sequence thereto, provided that said oligonucleotide is not a sequential subset of the nucleotide sequence encoding the Bovine 14-3-3 protein as shown in SEQ ID NO:3.

3. A probe comprising an oligonucleotide identical or complementary to the nucleotide sequence encoding the HME1 protein as shown in SEQ ID NO: 1, said oligonucleotide being at least 15 nucleotides in length, provided that said oligonucleotide is not a sequential subset of the nucleotide sequence encoding the Bovine 14-3-3 protein as shown in SEQ ID NO:3.

4. A method of determining the level of HME1 expression in a clinical sample of human tissue suspected of containing normal epithelial cells or epithelial cells in a state of neoplastic transformation, comprising:

providing an RNA preparation from said sample;

transferring the RNA preparation onto an immobilizing membrane;

contacting said membrane with the probe of claim 3 that is labeled with a signal under hybridizing conditions; and detecting duplex formation on said membrane by means of said signal.

5. A method of determining the level of HME1 expression in a clinical sample of human tissue suspected of containing normal epithelial cells or epithelial cells in a state of neoplastic transformation, comprising:

providing an RNA-containing preparation from said sample;

contacting said RNA-containing preparation with the probe of claim 3 that is labeled with a signal, whereby HME1 RNA in said preparation is bound to said probe;

digesting single-stranded nucleotide sequences in said preparation by means of a nuclease enzyme specific for said sequences to produce a digested preparation;

separating said digested preparation by electrophoresis to produce an electrophoretically separated sample; and determining the level of duplex formation in said electrophoretically separated sample by means of said signal-labelled probe.

6. The method of claim 5, comprising the further step of transferring said electrophoretically separated sample to a membrane prior to said determining step.

7. A method of detecting HME-1-expressing cells in a sample of tissue, comprising the steps of contacting ribonucleic acids in said tissue sample with the probe of claim 3, and detecting the presence or absence of an HME1 genetic sequence.

8. The isolated oligonucleotide of claim 1 being at least 100 nucleotides in length.

9. The isolated oligonucleotide of claim 2 being at least 100 nucleotides in length.

10. The probe of claim 3 being at least 100 nucleotides in length.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1245 base pairs
        ( B ) TYPE: nucleic acid
        ( C ) STRANDEDNESS: single
        ( D ) TOPOLOGY: linear ( i i ) MOLECULE TYPE: DNA (genomic)

(iii) HYPOTHETICAL: NO (iv) ANTI-SENSE: NO (xi) SEQUENCE DESCRIPTION: SEQ ID NO:1:

| | | | | | | |
|---|---|---|---|---|---|---|
| GCACGAGGCC | ATGGAGAGAG | CCAGTCTGAT | CCAGAAGGCC | AAGCTGGCAG | AGCAGGCCGA | 60 |
| ACGCTATGAG | GACATGGCAG | CCTTCATGAA | AGGCGCCGTG | GAGAAGGGCG | AGGAGCTCTC | 120 |
| CTGCGAAGAG | CGAAACCTGC | TCTCAGTAGC | CTATAAGAAC | GTGGTGGGCG | GCCAGAGGGC | 180 |
| TGCCTGGAGG | GTGCTGTCCA | GTATTGAGCA | GAAAAGCAAC | GAGGAGGGCT | CGGAGGAGAA | 240 |
| GGGGCCCGAG | GTGCGTGAGT | ACCGGGAGAA | GGTGGAGACT | GAGCTCCAGG | GCGTGTGCGA | 300 |
| CACCGTGCTG | GGCCTGCTGG | ACAGCCACCT | CATCAAGGAG | GCCGGGGACG | CCGAGAGCCG | 360 |
| GGTCTTCCAC | CTGAAGATGA | AGGGTGACTA | CTACCGCTAC | CTGGCCGAGG | TGGCCACCGG | 420 |
| TGACGACAAG | AAGCGCATCA | TTGACTCAGC | CCGGTCAGCC | TACCAGGAGG | CCATGGACAT | 480 |
| CAGCAAGAAG | GAGATGCCGC | CCACCAACCC | CATCCGCCTG | GGCCTGGCCC | TGAACTTTTC | 540 |
| CGTCTTCCAC | TACGAGATCG | CCAACAGCCC | CGAGGAGGCC | ATCTCTCTGG | CCAAGACCAC | 600 |
| TTTCGACGAG | GCCATGGCTG | ATCTGCACAC | CCTCAGCGAG | GACTCCTACA | AGACAGCAC | 660 |
| CCTCATCATG | CAGCTGCTGC | GAGACAACCT | GACACTGTGG | ACGGCCGACA | ACGCCGGGGA | 720 |
| AGAGGGGGGC | GAGGTTCCCC | AGGAGCCCCA | GAGCTGAGTG | TTGCCCGCCA | CCGCCCCGCC | 780 |
| CTGCCCTCCA | GTCCCCCACC | CTGCCGAGAG | GACTAGTATT | GTGGAGGGCC | CACCCTTCTC | 840 |
| CCCTAGGCGC | TGTTCTTGCT | CCCAAGGCTC | CGTGGAGAGG | GACTGCAGAC | TGAGGCCACC | 900 |
| TGGGCTGGGG | ATCCACTCTT | CTTGCAGCTG | TTGAGCGCAC | CTAACCACTG | GTCATGCCCC | 960 |
| CACCCCTGCT | CTCCGCACCC | GCTTCCTCCC | GACCCCAGGA | CCAGGCTACT | TCTCCCCTCC | 1020 |
| TCTTGCCTCC | CTCCTGCCCC | TGCTGCCTCT | GATCGTAGGA | ATTGAGGAGT | GTCCCCTTGT | 1080 |
| GGCTGTGAAC | TGGACAGTGC | AGGGGCTGGA | GATGGGGTGT | GTGTGTGTGT | GTGTGTGTGT | 1140 |
| GTGTGTGTGT | GTGCTCGCGC | GCCAGTGCAA | GACCGAGATT | GAGGGAAAGC | ATGTCTGCTG | 1200 |
| GGTGTGACCA | TGTTTCCTC | TCAATAAAGT | TGGGGTGTGA | CACTC | | 1245 |

(2) INFORMATION FOR SEQ ID NO:2:

(i) SEQUENCE CHARACTERISTICS:
        (A) LENGTH: 249 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:2:

```
Met Glu Arg Ala Ser Leu Ile Gln Lys Ala Lys Leu Ala Glu Gln Ala
 1               5                  10                  15

Glu Arg Tyr Glu Asp Met Ala Ala Phe Met Lys Gly Ala Val Glu Lys
                20                  25                  30

Gly Glu Glu Leu Ser Cys Glu Glu Arg Asn Leu Leu Ser Val Ala Tyr
            35                  40                  45

Lys Asn Val Val Gly Gly Gln Arg Ala Ala Trp Arg Val Leu Ser Ser
        50                  55                  60

Ile Glu Gln Lys Ser Asn Glu Glu Gly Ser Glu Glu Lys Gly Pro Glu
```

|     |     |     |     | 65  |     |     |     |     | 70  |     |     |     |     | 75  |     |     |     |     | 80  |
|-----|-----|-----|-----|-----|-----|-----|-----|-----|-----|-----|-----|-----|-----|-----|-----|-----|-----|-----|-----|
| Val | Arg | Glu | Tyr | Arg<br>85 | Glu | Lys | Val | Glu | Thr<br>90 | Glu | Leu | Gln | Gly | Val<br>95 | Cys |
| Asp | Thr | Val | Leu<br>100 | Gly | Leu | Leu | Asp | Ser<br>105 | His | Leu | Ile | Lys | Glu<br>110 | Ala | Gly |
| Asp | Ala | Glu | Ser<br>115 | Arg | Val | Phe | His<br>120 | Leu | Lys | Met | Lys | Gly<br>125 | Asp | Tyr | Tyr |
| Arg | Tyr<br>130 | Leu | Ala | Glu | Val | Ala<br>135 | Thr | Gly | Asp | Asp | Lys<br>140 | Lys | Arg | Ile | Ile |
| Asp<br>145 | Ser | Ala | Arg | Ser | Ala<br>150 | Tyr | Gln | Glu | Ala | Met<br>155 | Asp | Ile | Ser | Lys | Lys<br>160 |
| Glu | Met | Pro | Pro | Thr<br>165 | Asn | Pro | Ile | Arg | Leu<br>170 | Gly | Leu | Ala | Leu | Asn<br>175 | Phe |
| Ser | Val | Phe | His<br>180 | Tyr | Glu | Ile | Ala | Asn<br>185 | Ser | Pro | Glu | Glu | Ala<br>190 | Ile | Ser |
| Leu | Ala | Lys<br>195 | Thr | Thr | Phe | Asp | Glu<br>200 | Ala | Met | Ala | Asp | Leu<br>205 | His | Thr | Leu |
| Ser | Glu<br>210 | Asp | Ser | Tyr | Lys | Asp<br>215 | Ser | Thr | Leu | Ile | Met<br>220 | Gln | Leu | Leu | Arg |
| Asp<br>225 | Asn | Leu | Thr | Leu | Trp<br>230 | Thr | Ala | Asp | Asn | Ala<br>235 | Gly | Glu | Glu | Gly | Gly<br>240 |
| Glu | Val | Pro | Gln | Glu<br>245 | Pro | Gln | Ser | Glx |

( 2 ) INFORMATION FOR SEQ ID NO:3:

( i ) SEQUENCE CHARACTERISTICS:
    ( A ) LENGTH: 1696 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

| | | | | | |
|---|---|---|---|---|---|
| ACAGAGCGCC | GGGCGAGCCA | GCGAGAGGGC | GAGAGGCGCT | GCTTGCTGCC | TGCAGCCTCG | 60 |
| GCCGGCCGGC | AAGCCAGTGC | GCGTGCGCGG | CGGCGGCCTC | CGCGGCGACC | GGAGAGGACG | 120 |
| CGCGGGCGAG | CGAGCGGAGC | GGGAAGCGAG | GCCGGGCTCA | GCGACATGGG | GGACCGCGAG | 180 |
| CAGCTGCTGC | AGCGGGCGCG | GCTGGCCGAG | CAGGCGGAGC | GCTACGACGA | CATGGCCTCC | 240 |
| GCCATGAAGG | CGGTGACTGA | GCTCAATGAA | CCTCTCTCCA | ACGAAGACCG | AAACCTCCTC | 300 |
| TCCGTGGCCT | ACAAGAACGT | GGTTGGTGCC | CGGCGGTCTT | CCTGGAGGGT | CATCAGCAGC | 360 |
| ATCGAGCAGA | AGACCATGGC | TGATGGGAAT | GAGAAGAAGC | TGGAGAAGGT | GAAGGCCTAC | 420 |
| CGGGAGAAGA | TTGAGAAGGA | GCTGGAGACG | GTGTGCAACG | ACGTGCTGGC | GCTGCTGGAC | 480 |
| AAGTTCCTCA | TCAAGAACTG | CAATGACTTC | CAGTACGAGA | GCAAGGTCTT | CTACCTGAAG | 540 |
| ATGAAGGGCG | ACTACTACCG | CTACCTGGCC | GAGGTGGCTT | CTGGCGAGAA | GAAGAACAGT | 600 |
| GTGGTGGAGG | CCTCAGAGGC | GGCCTACAAG | GAAGCTTCG | AGATTAGCAA | GGAGCACATG | 660 |
| CAGCCCACAC | ACCCCATCCG | GCTGGGCCTG | GCCCTCAACT | TCTCCGTGTT | CTACTACGAG | 720 |
| ATCCAGAATG | CGCCTGAGCA | GGCCTGCCTC | CTAGCCAAAC | AAGCCTTCGA | CGACGCCATA | 780 |
| GCCGAGCTGG | ACACACTAAA | CGAGGATTCC | TATAAGGACT | CCACGCTCAT | CATGCAGCTG | 840 |

-continued

| | | | | | |
|---|---|---|---|---|---|
| CTGCGAGACA | ACCTCACCCT | CTGGACGAGC | GACCAGCAGG | ACGAGGAAGC | CGGAGAAGGC | 900 |
| AACTGAGCGC | CTTGGCCCGC | CCCGCCCCCG | CCCCATCACC | ACCAGTCCCC | TCTCGCCACA | 960 |
| CTCACTAAGT | ATCCAGTGCT | CAACCTATCT | GTACGGCAGC | ACAGCTACTC | AGACCTGCTG | 1020 |
| TCCGCCCCCG | GGAAGCAGTT | CCAGATAAAT | TAATTCATGG | GCATCGCTGG | ACTGACGGTT | 1080 |
| GCTTTGAGCC | CACAGGAGCT | CCCTTTTTGG | ATCGTGCAGA | CAGGTGCGTT | CTGAAGGAGG | 1140 |
| CATTGTCGTT | TGCTTGCCTG | TCTAGGTGAA | TTGCAGGCGA | AAGCCTCAGA | AAGTTAGAGA | 1200 |
| GGAGAATTAG | CCACACAGGC | TACAGTTGGT | ATTTAAATGG | TCCACTTCAA | ACCAGCTGCT | 1260 |
| AGTGTTTTGT | TAAAGCAGTA | CATCTGTGCA | TGCAAAAGTG | AATTCACCCC | TCCCTCTTCT | 1320 |
| TTCTTAGCTA | ATGGAAAACC | ATTAAGGGAA | GCTGGAACGA | GAGACCACTT | GCTCCTTTCC | 1380 |
| ATCAGCTTAA | TAATTAACTT | TAACGTGAGG | TTTCAGTAGC | ACCTTGTTCG | CCTCTTTAAA | 1440 |
| TTATGACGTG | CACAAACCTT | CTTTTCAATG | CAATGCATCT | AAAGTTTTGA | TACCTGTAAC | 1500 |
| TTTTTTTTTT | GGTTGCAATT | GTTAAGAAT | CATGGATTTA | TTTTTGTAA | CTCTTTGGCT | 1560 |
| ATCGTCCTTG | TGTATCCTGA | CAGCGCCATG | TGTGTCAGCC | CATGTCAATC | AAGATGGGTG | 1620 |
| ATTATGAAAT | GCCAGACTCC | TAAATTAAAT | GTTTGGAAT | TCAGTGGGTA | AATAAAAATG | 1680 |
| CTGCTTTGGG | GATATT | | | | | 1696 |

( 2 ) INFORMATION FOR SEQ ID NO:4:

( i ) SEQUENCE CHARACTERISTICS:
        ( A ) LENGTH: 246 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

```
Met Gly Asp Arg Glu Gln Leu Leu Gln Arg Ala Arg Leu Ala Glu Gln
 1               5                  10                  15

Ala Glu Arg Tyr Asp Asp Met Ala Ser Ala Met Lys Ala Val Thr Glu
            20                  25                  30

Leu Asn Glu Pro Leu Ser Asn Glu Asp Arg Asn Leu Leu Ser Val Ala
        35                  40                  45

Tyr Lys Asn Val Val Gly Ala Arg Arg Ser Ser Trp Arg Val Ile Ser
    50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
                85                  90                  95

Cys Asn Asp Val Leu Ala Leu Leu Asp Lys Phe Leu Ile Lys Asn Cys
            100                 105                 110

Asn Asp Phe Gln Tyr Glu Ser Lys Val Phe Tyr Leu Lys Met Lys Gly
        115                 120                 125

Asp Tyr Tyr Arg Tyr Leu Ala Glu Val Ala Ser Gly Glu Lys Lys Asn
    130                 135                 140

Ser Val Val Glu Ala Ser Glu Ala Ala Tyr Lys Glu Ala Phe Glu Ile
145                 150                 155                 160

Ser Lys Glu His Met Gln Pro Thr His Pro Ile Arg Leu Gly Leu Ala
```

```
                                    165                              170                                   175

Leu  Asn  Phe  Ser  Val  Phe  Tyr  Tyr  Glu  Ile  Gln  Asn  Ala  Pro  Glu  Gln
                           180                        185                      190

Ala  Cys  Leu  Leu  Ala  Lys  Gln  Ala  Phe  Asp  Asp  Ala  Ile  Ala  Glu  Leu
                      195                        200                           205

Asp  Thr  Leu  Asn  Glu  Asp  Ser  Tyr  Lys  Asp  Ser  Thr  Leu  Ile  Met  Gln
                 210                      215                      220

Leu  Leu  Arg  Asp  Asn  Leu  Thr  Leu  Trp  Thr  Ser  Asp  Gln  Gln  Asp  Glu
            225                      230                      235                           240

Glu  Ala  Gly  Glu  Gly  Asn
                                245
```

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

```
TACCTGCGGT  AGTTCTTCTT  CTACGTCTAC                                              30
```